US008309028B2

(12) United States Patent
Raguse et al.

(10) Patent No.: US 8,309,028 B2
(45) Date of Patent: Nov. 13, 2012

(54) CHEMIRESISTOR FOR USE IN CONDUCTING ELECTROLYTE SOLUTION

(75) Inventors: Burkhard Raguse, Gordon (AU); Edith Chow, Huntleys Cove (AU)

(73) Assignee: Commonwealth Scientific and Industrial Research Organisation (AU)

( * ) Notice: Subject to any disclaimer, the term of this patent is extended or adjusted under 35 U.S.C. 154(b) by 208 days.

(21) Appl. No.: 12/525,253

(22) PCT Filed: Feb. 1, 2008

(86) PCT No.: PCT/AU2008/000117
§ 371 (c)(1),
(2), (4) Date: Mar. 11, 2010

(87) PCT Pub. No.: WO2008/092210
PCT Pub. Date: Aug. 7, 2008

(65) Prior Publication Data
US 2010/0276302 A1      Nov. 4, 2010

(30) Foreign Application Priority Data

Feb. 2, 2007   (AU) ................................ 2007900501

(51) Int. Cl.
*G01N 15/06* (2006.01)
*G01N 33/00* (2006.01)
*G01N 33/48* (2006.01)

(52) U.S. Cl. ........ 422/82.02; 422/50; 422/83; 422/68.1; 422/82.01; 436/43; 436/149; 436/150

(58) Field of Classification Search ............ 422/50, 422/83, 68.1, 82.01, 82.02; 436/43, 149, 436/150
See application file for complete search history.

(56) References Cited

U.S. PATENT DOCUMENTS 4,539,061 A *   9/1985 Sagiv ............................ 156/278
(Continued)

FOREIGN PATENT DOCUMENTS
EP    1612547 A1    1/2006
(Continued)

OTHER PUBLICATIONS

International Search Report and Written Opinion for PCT Application No. PCT/AU2008/000117, 5 pages, Apr. 29, 2008.
(Continued)

*Primary Examiner* — Brian J Sines
(74) *Attorney, Agent, or Firm* — Brinks Hofer Gilson & Lione

(57) ABSTRACT

The present invention provides a chemiresistor-based sensor for measuring the presence or amount of analyte in an electrolyte solution; said chemiresistor comprising (i) a chemiresistor film wherein the impedance of said nanoparticle film changes in the presence of an analyte; and (ii) two electrically conducting electrodes in electrical contact with said nanoparticle film; wherein said electrically conducting electrodes are adapted to be connected to a device for measuring the impedance of said chemiresistor film under a voltage signal and wherein the impedance of the double layer capacitor formed by the two electrically conducting electrodes in the presence of the electrolyte solution, is larger than the impedance of the chemiresistor film either before or after exposure of the chemiresistor film to the analyte. A method of using said chemiresistor-based sensor to measure the presence or amount of analyte is also provided. Further provided is a method of determining the partition coefficient of an analyte using said chemiresistor-based sensor.

16 Claims, 10 Drawing Sheets

U.S. PATENT DOCUMENTS

| | | | |
|---|---|---|---|
| 4,636,767 A * | 1/1987 | Barger et al. | 338/34 |
| 4,900,405 A * | 2/1990 | Otagawa et al. | 205/781 |
| 4,992,244 A * | 2/1991 | Grate | 422/98 |
| 5,071,770 A * | 12/1991 | Kolesar, Jr. | 436/151 |
| 5,321,146 A * | 6/1994 | Royster et al. | 556/57 |
| 5,919,576 A * | 7/1999 | Hui et al. | 428/545 |
| 6,017,440 A * | 1/2000 | Lewis et al. | 205/777.5 |
| 6,458,327 B1 | 10/2002 | Vossmeyer | |
| 6,773,926 B1 * | 8/2004 | Freund et al. | 436/149 |
| 7,112,304 B2 * | 9/2006 | Starling et al. | 422/83 |
| 2002/0132361 A1 * | 9/2002 | Vossmeyer et al. | 436/151 |
| 2003/0109056 A1 | 6/2003 | Vossmeyer et al. | |
| 2004/0029288 A1 * | 2/2004 | Snow et al. | 436/149 |
| 2004/0200722 A1 * | 10/2004 | Starling et al. | 204/403.01 |
| 2005/0150778 A1 | 7/2005 | Lewis et al. | |

FOREIGN PATENT DOCUMENTS

| | | |
|---|---|---|
| WO | WO 00/00808 | 1/2000 |

OTHER PUBLICATIONS

Mathias Brust, Merryl Walker, Donald Bethell, David J. Schiffrin and Robin Whyman, *Synthesis of thiol-derivatised gold nanoparticles in a two-phase Liquid-Liquid system*, J. Chem. Soc., Chem. Commun., 1994, 801-802.

Brett J. Doleman, Mark C. Lonergan, Erik J. Severin, Thomas P. Vaid, and Nathan S. Lewis, *Quantitative Study of the Resolving Power of Arrays of Carbon Black-Polymer Composites in Various Vapor-Sensing Tasks*, Anal. Chem., 1998, vol. 70, 4177-4190.

Stephen D. Evans, Simon R. Johnson, Yaling L. Cheng and Tiehan Shen, *Vapour sensing using hybrid organic-inorganic nanostructured materials*, J. Mater. Chem., 2000, vol. 10, 183-188.

David I. Gittins and Frank Caruso, *Spontaneous Phase Transfer of Nanoparticulate Metals from Organic to Aqueous Media*, Angew. Chemie Int. Ed. 2001, vol. 40, 3001-3004.

Mark C. Lonergan, Erik J. Severin, Brett J. Doleman, Sara A. Beaber, Robert H. Grubbs, and Nathan S. Lewis, *Array-Based Vapor Sensing Using Chemically Sensitive, Carbon Black-Polymer Resistors*, Chem. Mater., 1996, vol. 8, 2298-2312.

Paul Ruelle, *The n-octanol and n-hexane/water partition coefficient of environmentally relevant chemicals predicted from the mobile order and disorder (MOD) thermodynamics*, Chemosphere, 2000, vol. 40, 457-512.

Gregory A. Sotzing, Jennifer N. Phend, Robert H. Grubbs, and Nathan S. Lewis, *Highly Sensitive Detection and Discrimination of Biogenic Amines Utilizing Arrays of Polyaniline/Carbon Black Composite Vapor Detectors*, Chem. Mater., 2000, vol. 12, 593-595.

Hank Wohltjen and Arthur W. Snow, *Colloidal Metal-Insulator-Metal Ensemble Chemiresistor Sensor*, Anal. Chem., 1998, vol. 70, 2856-2859.

\* cited by examiner

CHEMIRESISTOR FOR USE IN CONDUCTING ELECTROLYTE SOLUTION

This application is a filing under 35 U.S.C. §371 of International Patent Application PCT/AU2008/000117, filed Feb. 1, 2008, which claims priority to Australian application no. AU 2007900501, filed Feb. 2, 2007.

FIELD OF THE INVENTION

The present invention relates to chemical sensors, in particular to chemiresistors that are capable of detecting analytes in a liquid environment that potentially has a high ionic conductivity.

BACKGROUND OF THE INVENTION

Chemiresistors are a class of chemical sensors wherein the electrical resistance of a sensing element changes in response to the presence or absence of a chemical species. Chemiresistors are attractive for use as chemical sensors as it is relatively easy to measure and record small changes in electrical resistance.

Chemiresistors and arrays of chemiresistors for determining the level of analytes in the vapour or gas phase are well established in the art. One method of realising such a chemiresistor is to mix a conducting material such as carbon black with a conducting or non-conducting polymer (Lonergan et al., Chem Mater., 1996, 8, 2298; Doleman et al, Anal. Chem., 1998, 70, 4177; Sotzing et al, Chem Mater., 2000, 12, 593). Thin films of such a matrix are then prepared with appropriate electrodes being attached to each end of the thin film. This forms the chemiresistor. The amount of carbon black and the properties of the polymers are adjusted so that a measurable resistance can be determined. When exposed to a gas or vapour that contains an amount of analyte, the analyte is adsorbed by the carbon black/polymer matrix, which subsequently swells. The swelling causes the conducting particles to move further apart leading to an increase in resistance of the chemiresistor which can be determined by standard ac or dc methods.

More recently, thin films of gold nanoparticles coated with a variety of different monolayers of molecules have been used as chemiresistors. For instance Wohtljen and Snow (Anal. Chem., 1998, 70, 2856) describe gold nanoparticle thin films prepared on interdigitated electrodes, based on 2 nm diameter gold clusters encapsulated by monolayers of 1-octanethiol. On exposure to organic vapours such as toluene in nitrogen carrier gas reversible changes in the resistance of the thin film were observed.

A variety of compounds can be used to coat the conductive nanoparticles. For instance Vossmeyer et al. (US 2003/0109056 A1) teaches the use of dendrimers to coat gold nanoparticles to produce thin film chemiresistors with particular selectivities towards different analytes such as toluene, propanol or water in the vapour phase. S. D. Evans et al (J. Mater. Chem. 2000, 8, 183) uses p-thiophenol derivatives to encapsulate the gold nanoparticles and to modify the chemiresistor behaviour. Lewis et al (US 2005/0150778 A1) teaches the use of amine functionalized polymers as coating for carbon black composites to detect volatile fatty acids.

Additionally, Lewis et al (WO 00/00808) teaches the use of arrays of nanoparticle films as chemical sensors. Baso et al (EP 1612547 A1) teaches the use of inkjet printing to produce arrays of sensors based on metallic nanoparticles.

The above disclosures in general teach methods of using such chemiresistors for detecting the presence of an analyte in the gas or vapour phase. However, the above disclosures do not teach how to use conducting nanoparticle based chemiresistors in an ionically conductive liquid phase in particular in an ionically conductive aqueous liquid phase (i.e. an electrolyte solution). In fact, Starling et al US 2004/0200722 A1 teach that "surface moisture effectively creates a bypass resistor in parallel resistance with the sensor probe. This bypass resistor typically desensitizes the performance of the sensor". In U.S. Pat. No. 6,458,327 B1 Vossmeyer et al teaches the use of bifunctional and multifunctional ligands to produce a nanoparticle film that can be used as a chemical sensor. Vossmeyer also teaches that the simple chemiresistor structure described by Wohtljen and Snow (Anal. Chem., 1998, 70, 2856) "may however not be suitable for detection in the liquid phase due to its structure". In order to produce a nanoparticle film structure suitable to function as a liquid phase sensor, Vossmeyer describes the use of nanoparticle films as part of a bipolar transistor structure or as part of a resonant tunnelling device. However, the production of such bipolar transistor or resonant tunnelling devices increases the complexity of the sensor device to an undesirable level compared to that of a simple chemiresistor.

SUMMARY OF THE INVENTION

The present inventors have now determined that by controlling the ratio of the chemiresistor film impedance to the impedance due to the double layer capacitance of the total electrode surface in contact with the electrolyte solution, a conductive nanoparticle based chemiresistor can be produced that can directly sense analyte in ionically conductive aqueous solutions without having to resort to bipolar transistor or resonant tunnelling device structures.

The present inventors have further determined that by providing a thin dielectric layer between the contacts and the chemiresistor thin film, the effective double layer capacitance may be further reduced, thus increasing the impedance without significantly affecting the chemiresistor resistance measurement in response to an analyte.

The present inventors have further determined that by appropriate selection of ligands used to coat the nanoparticles, the response of the chemiresistor towards organic analytes can be correlated with hexane/water or octanol/water partition coefficients.

In a first aspect, the present invention provides a chemiresistor-based sensor for measuring the presence or amount of analyte in an electrolyte solution; said chemiresistor comprising
 (i) a chemiresistor film wherein the impedance of said nanoparticle film changes in the presence of an analyte; and
 (ii) two electrically conducting electrodes in electrical contact with said nanoparticle film;
 wherein said electrically conducting electrodes are adapted to be connected to a device for measuring the impedance of said nanoparticle film under a voltage signal and wherein the impedance of the double layer capacitor formed by the two electrically conducting electrodes in the presence of the electrolyte solution, is larger than the impedance of the nanoparticle film either before or after exposure of the nanoparticle film to the analyte.

The chemiresistor film is preferably a nanoparticle film.

Preferably, the chemiresistor-based sensor does not comprise a bipolar transistor device or resonant tunnelling device.

In a second aspect, the present invention provides a method of measuring the presence or amount of analyte in an electrolyte solution using a chemiresistor-based sensor of the first aspect, the method comprising the steps of:

(i) contacting the chemiresistor film with the electrolyte solution; and
(ii) measuring the change in the impedance of the chemiresistor film.

Preferably, the invention of the second step comprises the additional step of:
(iii) comparing the value of the measurement in step (ii) with measurement(s) of the change in impedance of the chemiresistor film in the presence of said analyte at one or more known concentrations to thereby determine the amount of analyte in said electrolyte solution.

In a third aspect, the present invention provides a method for determining the partition coefficient of an analyte using the chemiresistor-based sensor of the first aspect, said method comprising the steps of:
(i) contacting said chemiresistor film with two or more solutions of said analyte wherein said two or more solutions of said analyte are of known but different concentrations;
(ii) measuring the change in impedance of said chemiresistor film for each of said two or more solutions;
(iii) fitting a line to the log-log plot of change in the impedance of the nanoparticle film versus concentration of said analyte;
(iv) calculating the value of the logarithm of the slope of said fitted line;
(v) comparing the value of the logarithm of the slope of said fitted line to a standard curve correlating the logarithm of said slope of said fitted line to the logarithm of the partition coefficient to thereby determine said partition coefficient of said analyte.

The standard curve can be constructed by carrying out steps (i) to (iv) for two or more analytes having known partition coefficients.

DETAILED DESCRIPTION OF THE INVENTION

In a first aspect, the present invention provides a chemiresistor-based sensor for measuring the presence or amount of analyte in an electrolyte solution; said chemiresistor comprising
(i) a chemiresistor film wherein the impedance of said chemiresistor film changes in the presence of an analyte; and
(ii) two electrically conducting electrodes in electrical contact with said chemiresistor film;
wherein said electrically conducting electrodes are adapted to be connected to a device for measuring the impedance of said chemiresistor film under a voltage signal and wherein the impedance of the double layer capacitor formed by the two electrically conducting electrodes in the presence of the electrolyte solution, is larger than the impedance of the chemiresistor film either before or after exposure of the chemiresistor film to the analyte.

The chemiresistor film is preferably a nanoparticle film.

In a second aspect, the present invention provides a method of measuring the presence or amount of analyte in an electrolyte solution using a chemiresistor of the first aspect, the method comprising the steps of:
(i) contacting the nanoparticle film with the electrolyte solution; and
(ii) measuring the change in the impedance of the nanoparticle film.

Preferably, the invention of the second step comprises the additional step of:
(iii) comparing the value of the measurement in step (ii) with measurement(s) of the change in impedance of the nanoparticle film in the presence of said analyte at one or more known concentrations to thereby determine the amount of analyte in said electrolyte solution.

It is preferred that the impedance of the electrically conductive electrodes in electrolyte solution, but in the absence of the chemiresistor film, is twice as large as the impedance of the chemiresistor film, more preferably 5 times larger, most preferably more than ten times larger.

In one embodiment, the voltage signal is a variable voltage signal. Preferably, the variable voltage signal is a sinusoidal alternating current signal.

Preferably, the frequency of the alternating current is below 100 Hz to dc, more preferably between 10 Hz and 0.1 Hz, most preferably at 1 Hz.

In another embodiment, the voltage signal is a constant voltage signal (ie direct current or dc).

Figure 1:
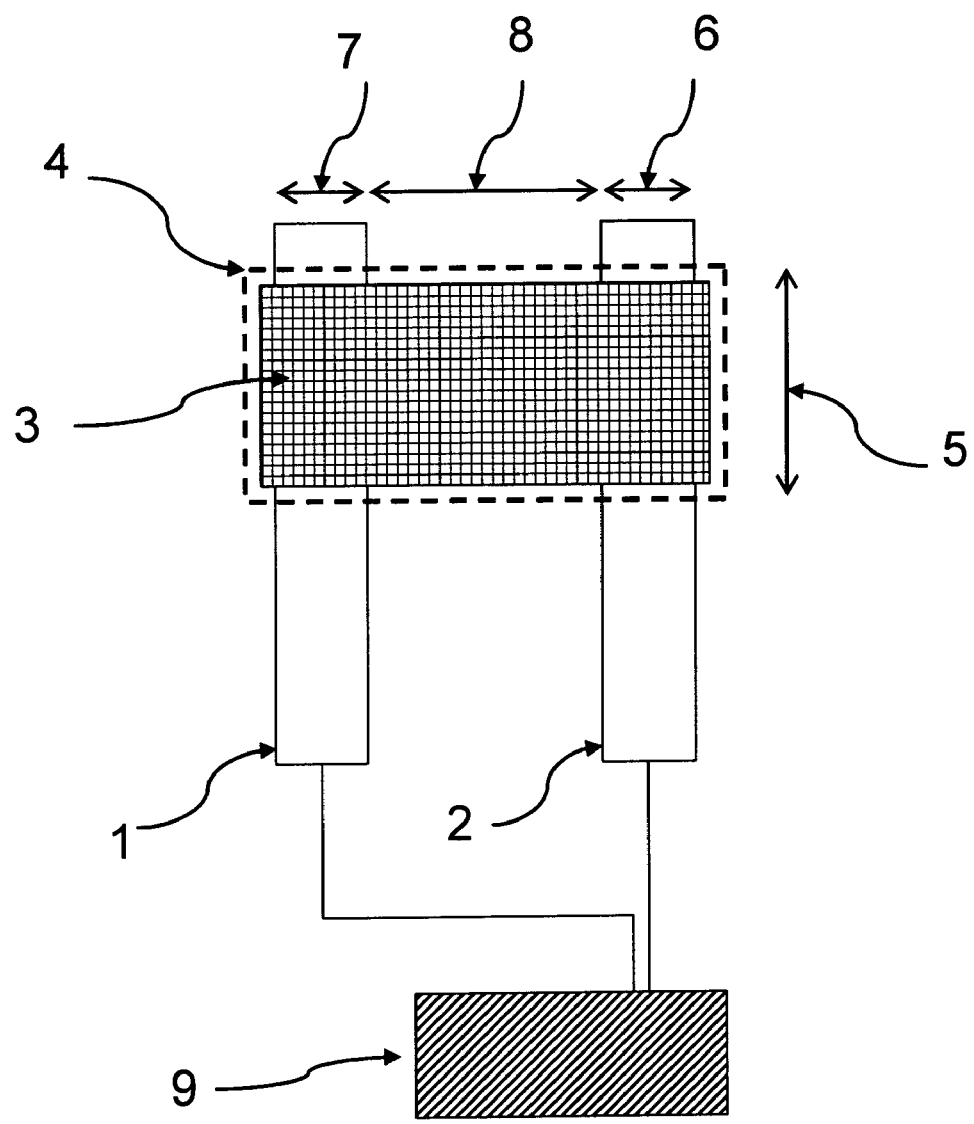
FIG. 1 illustrates an embodiment of a chemiresistor-based sensor, consisting of a thin film of chemiresistive material in contact with two electrically conductive contact pads and showing the area of the chemiresistor exposed to the electrolyte solution.

In order to simplify the description of the present invention reference is made to FIG. 1. FIG. 1 shows a simplified, schematic diagram (top view) of a typical chemiresistor layout. In this device the thin film chemiresistor element 3 is connected to a resistance or impedance measuring device 9 via two electrically conductive electrode pads 1 and 2. The area of the chemiresistor 3 and the area of the electrically conductive electrode pads 1 and 2 that are exposed to the electrolyte solution is indicated by the dashed line 4.

The critical dimensions for the present invention of the conductive pads 1 and 2 are the width, 6 and 7, and the length 5 that define the area of the electrically conductive electrode pads that are potentially exposed to the electrolyte solution. For a simple metal electrode, the double layer capacitance (Cdl) of the electrically conductive electrode pads area when immersed in electrolyte solution is approximated by Equation 1.

$$Cdl = \frac{\varepsilon \varepsilon_0 A}{d} \qquad \text{EQUATION 1}$$

In Equation 1, $\varepsilon_0$ is the permittivity of free space, $\varepsilon$ is the dielectric constant of the medium between the two capacitor plates (in the case of water this is approximately 80), d is the distance between two capacitor plates which in this case is determined by the distance of closest approach of the ions in the electrolyte solution (for example as described by the theories of Helmholtz or Gouy-Chapmann) and A is the area of the capacitor plate. Typical experimentally obtained values for the Cdl for a bare gold electrode are between 10-40 µF/cm$^2$.

In the present case A is equivalent to the area of the electrically conductive electrode pads 1 or 2 multiplied by the fraction of area accessible to the electrolyte after taking into account the amount of area occluded by the porous thin film chemiresistor deposited on top of the conductive pad. However, given that the nanoparticle based chemiresistor has a certain electrical conductivity and if the nanoparticle film is porous, then the apparent surface area may in fact be larger than the simple geometric surface area, that is the area above the contact pads acts as a highly porous conductive electrode. This would have the effect of increasing the effective capacitance. It should be noted that Equation 1 describes an ideal capacitor, porous electrodes or electrodes with significant surface roughness deviate from ideality and may be better described using constant phase elements.

It is known in the art that when measuring the impedance of a capacitor, and plotting the results in the form of the well known Bode plot format, that a plot of the log of absolute impedance versus the log of frequency has a slope of −1. This relationship is described in Equation 2.

$$|Z| = \frac{1}{2\pi fC}$$

In equation 2, |Z| is the absolute value of impedance (ohms), f is the frequency (Hz), C is the capacitance (in Farads) being measured. As can be seen as the frequency decreases the impedance increases and additionally the smaller the capacitance the larger the impedance.

From a theoretical standpoint it is therefore possible to calculate an estimate of the double layer capacitance of the contact pads and therefore to obtain an estimate of the absolute impedance value of such a capacitor at a particular frequency. It is of course possible and generally preferable to obtain the actual values of the impedance using techniques such as electrochemical impedance spectroscopy.

The resistance of the nanoparticle chemiresistor thin film is approximated in the structure shown in FIG. 1 by the length 8, width (approximately equal to 5) and height (not shown) of the thin film and by the resistivity of the material from which the thin film chemiresistor is formed. Obviously, by definition, the actual value of the resistance will vary depending on the level of exposure of the chemiresistor to the analyte. Typically nanoparticle based chemiresistors may have resistance of the order of 10's of kilo-ohms, through to 10's of Mega-ohms or higher. It should also be noted that the value of resistance of a resistor does not vary with frequency.

The resistivity of an electrolyte solution can vary significantly. For instance, highly purified water may have a resistivity of 18 Mohm cm, whereas a 1M KCl solution has a resistivity of approximately 9 ohm cm and seawater has a resistivity of approximately 20 ohm cm at 25° C. This could lead to a solution resistances of a few ohms between contact pad electrodes 1 and 2 in FIG. 1 when the chemiresistor is placed in relatively concentrated electrolyte solution.

Therefore, in order to produce a nanoparticle based chemiresistor that functions in electrolyte solution the three critical criteria of the chemiresistor sensor are that firstly, the electrically conductive electrode pad area (5 by 6 and 5 by 7) exposed to the electrolyte must be small enough, such that the capacitance is small enough and such that the impedance is large enough compared to the resistance of the chemiresistor film and secondly that the distance 8 between the two electrically conductive electrode pads 1 and 2 is also small enough such that the resistance of the chemiresistor is less that the impedance of capacitor formed by the electrically conductive electrode pads, and thirdly that the measurements are performed at a low enough frequency such that the impedance of the capacitor formed by the electrically conductive electrode pads is greater than the resistance of the nanoparticle chemiresistor.

Figure 2:
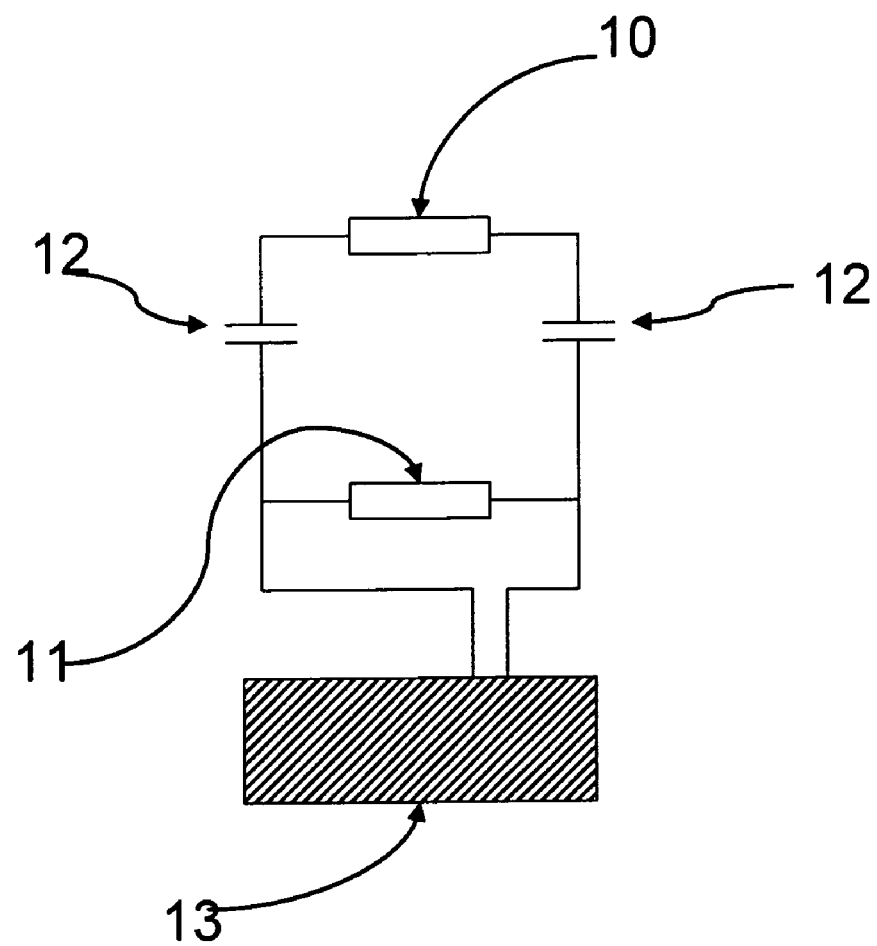
FIG. 2 shows a schematic of an equivalent circuit of the chemiresistor-based sensor when placed in an electrolyte solution.

The basic principle of the present invention may also be more clearly seen through examination of the simplified circuit analysis of the present nanoparticle chemiresistor sensor as shown in FIG. 2. As can be seen the nanoparticle chemiresistor 11 is in parallel to the electrolyte resistance 10. However, importantly these two resistors 10 and 11 are effectively decoupled from each other by the Cdl 12. This means that when the low frequency impedance of the circuit is measured by an apparatus such as an impedance bridge 13, the Cdl present an effectively very high impedance and hence the overall impedance of 10 and 12 is significantly higher than that of 11 and hence only changes in 11 are effectively measured.

The resistance or impedance of the chemiresistor may be determined by a number of standard methods known to those skilled in the art. These may include direct current (dc) or alternating current (ac) methods including the use of various shaped voltage waveforms such as pulse, double or multiple pulse, square-wave, triangle wave, staircase, sine wave.

In the case where a direct current (dc) measurement is made, that is, where a constant voltage is applied to the chemiresistor and the current is measured over time, it is preferred that the chemiresistor sensor is firstly exposed to an aqueous solution that does not contain the analyte until the Cdl 12 have essentially been charged and the current flow due to charging of the capacitors has fallen to a level low enough to be able to detect changes in the resistance of the nanoparticle film exposed to the aqueous solution, and then subsequently exposed to the aqueous test solution containing the analyte to be determined.

Preferably the impedance of the chemiresistor sensor is determined by impedance spectroscopy at a single frequency or at multiple frequencies. Standard apparatus may be used that uses sine waves or that uses pulse methods to determine the low frequency characteristics of the chemiresistor sensor.

Preferably ac impedance spectroscopy is used to determine the impedance of the chemiresistor sensor at low frequencies, preferably below 100 Hz to dc, more preferably between 10 Hz and 0.1 Hz, most preferably at 1 Hz.

At the preferred low frequency used to measure the resistance characteristics of the chemiresistor it is preferred that the impedance of the electrically conductive electrode pads in electrolyte solution, but in the absence of the chemiresistor thin film is twice as large as that when the chemiresistor thin film is deposited across the electrodes, more preferably 5 times larger, most preferably more than ten times larger.

Figure 3A:
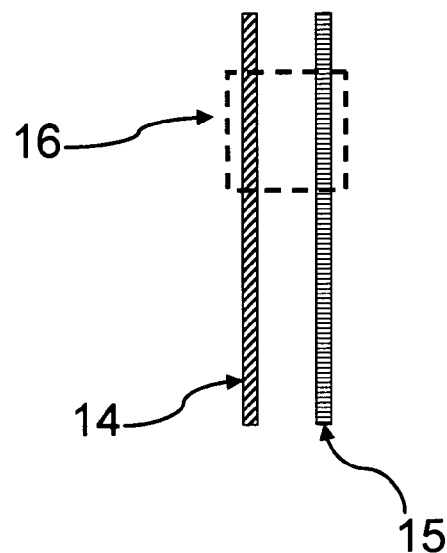
FIG. 3 shows a schematic of four different electrode configurations.

It is preferred that the electrically conductive electrode pads are made from two or more parallel band electrodes. A suitable arrangement is shown in FIG. 3a where 14 and are two conductive electrodes that are at least partially coated with a chemiresistor film 16.

In the case where the electrodes are made from 1 or more sets of band electrodes it is preferred that the distance between adjacent bands (8) is between 10 nm and 10 microns in width and that the width of the electrically conductive electrode pads (6, 7) is between 10 nm and 10 microns.

More preferably in the case where the electrodes are made from 1 or more sets of band electrodes it is preferred that the distance between adjacent bands (8) is between 100 nm and 5 microns in width and that the width of the electrically conductive electrode pads (6, 7) is between 100 nm and 5 microns.

Most preferably in the case where the electrodes are made from 1 or more sets of band electrodes it is preferred that the distance between adjacent bands (8) is between 100 nm and 1 micron in width and that the width of the electrically conductive electrode pads (6, 7) is between 100 nm and 1 micron.

Figure 3B:
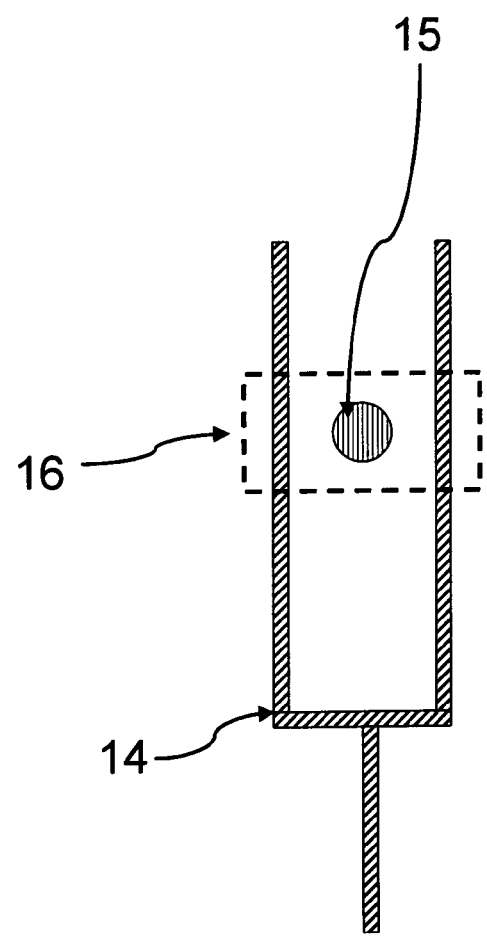
Figure 3C:
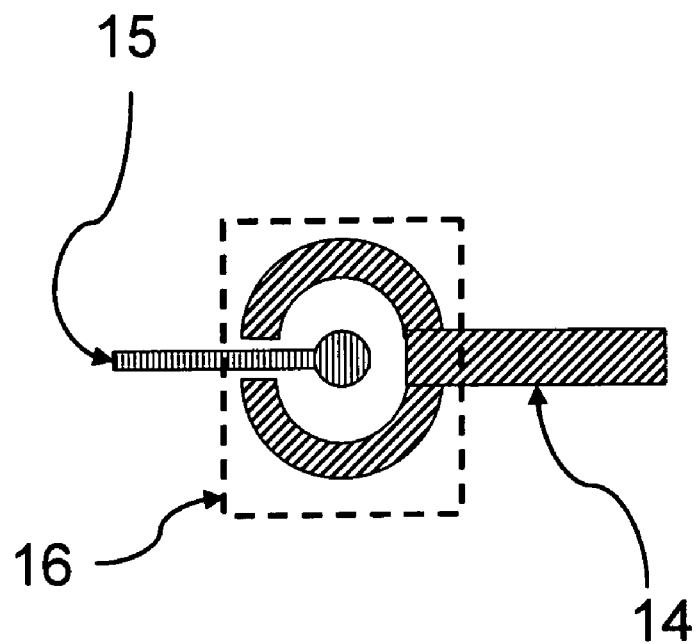
Figure 3D:
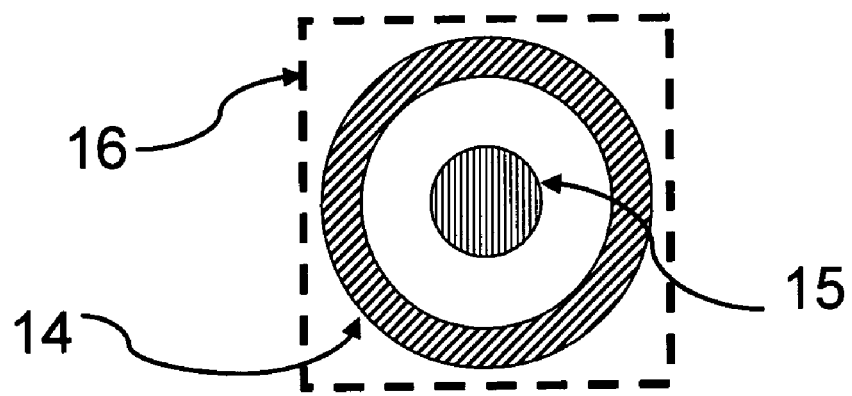
Figure 4:
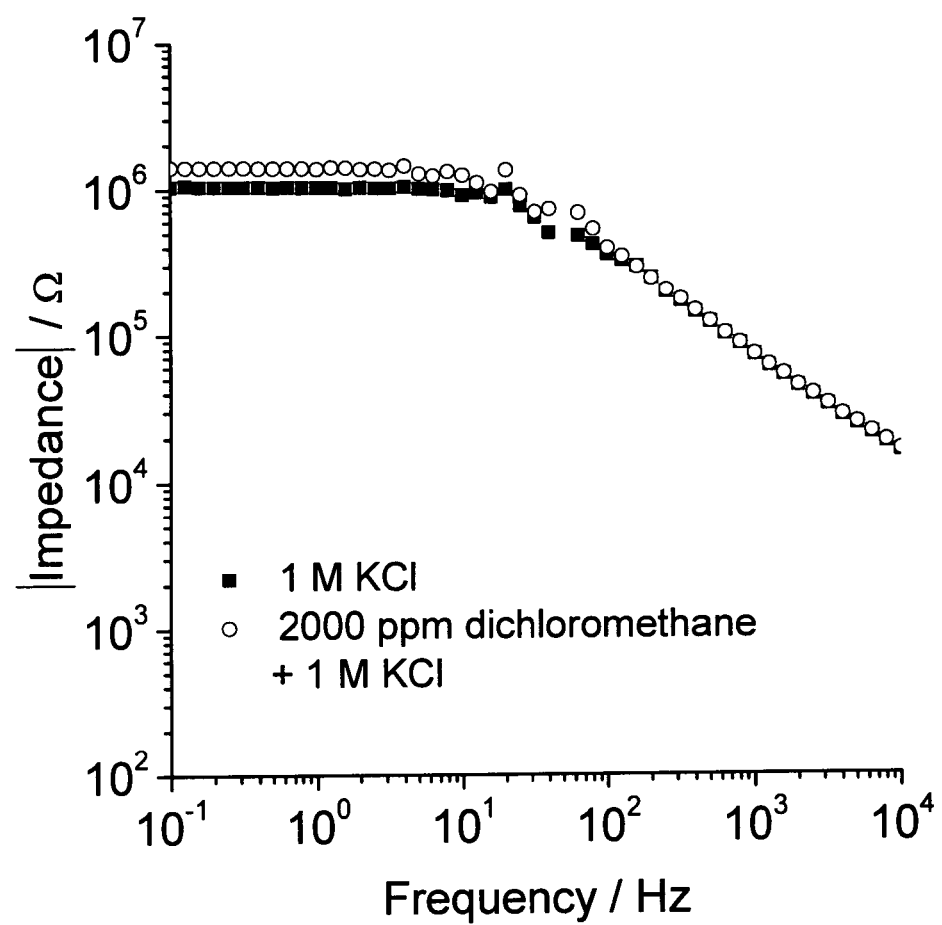
FIG. 4 shows the Bode (magnitude) plot obtained in 1 M KCl using chemiresistor band microelectrodes prepared according to example 3, in the absence of dichloromethane (closed squares) and in the presence of 2000 ppm dichloromethane (open circles).
Figure 5:
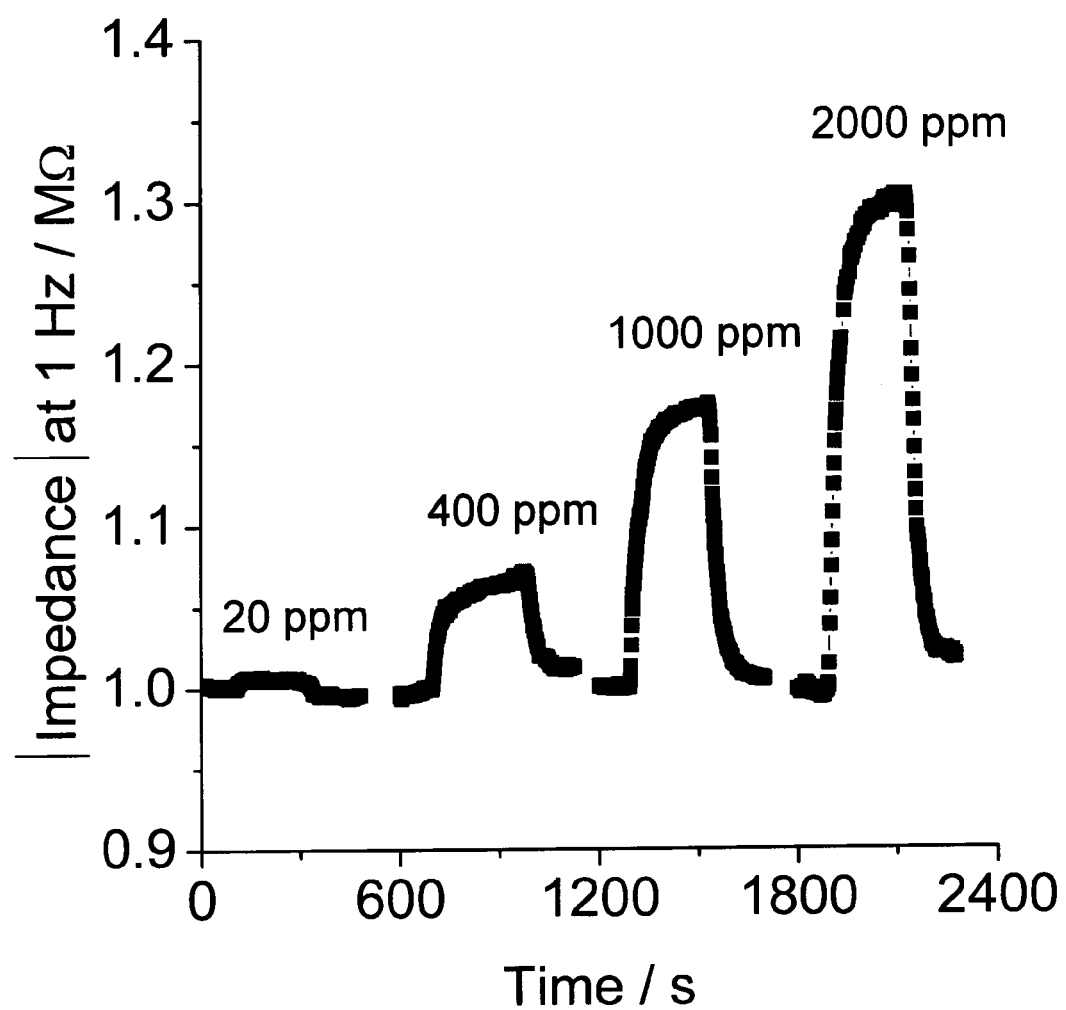
FIG. 5 shows the response curves of chemiresistor band microelectrodes electrodes prepared according to example 3, to different concentrations of dichloromethane (20 ppm, 400 ppm, 1000 ppm and 2000 ppm) as a function of time.
Figure 6:
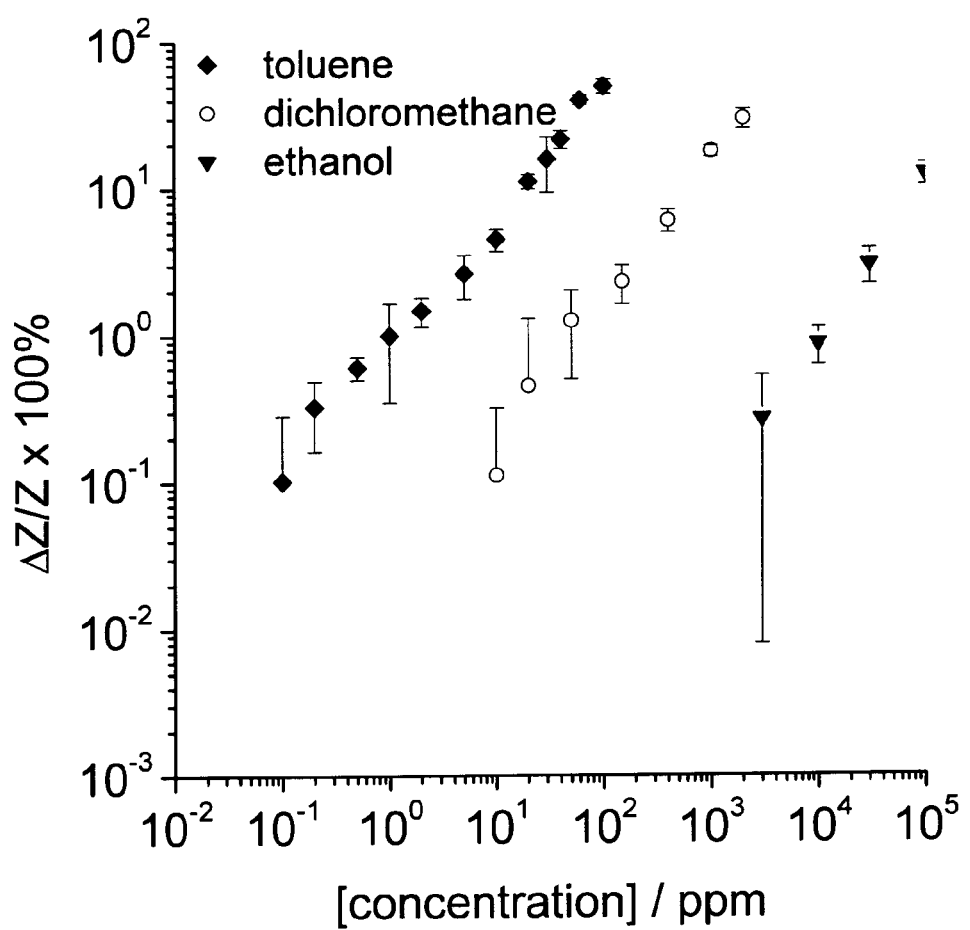
FIG. 6 shows the relative change in impedance of chemiresistor band microelectrodes prepared according to examples 3, as a function of concentration of dichloromethane, ethanol and toluene.
Figure 7:
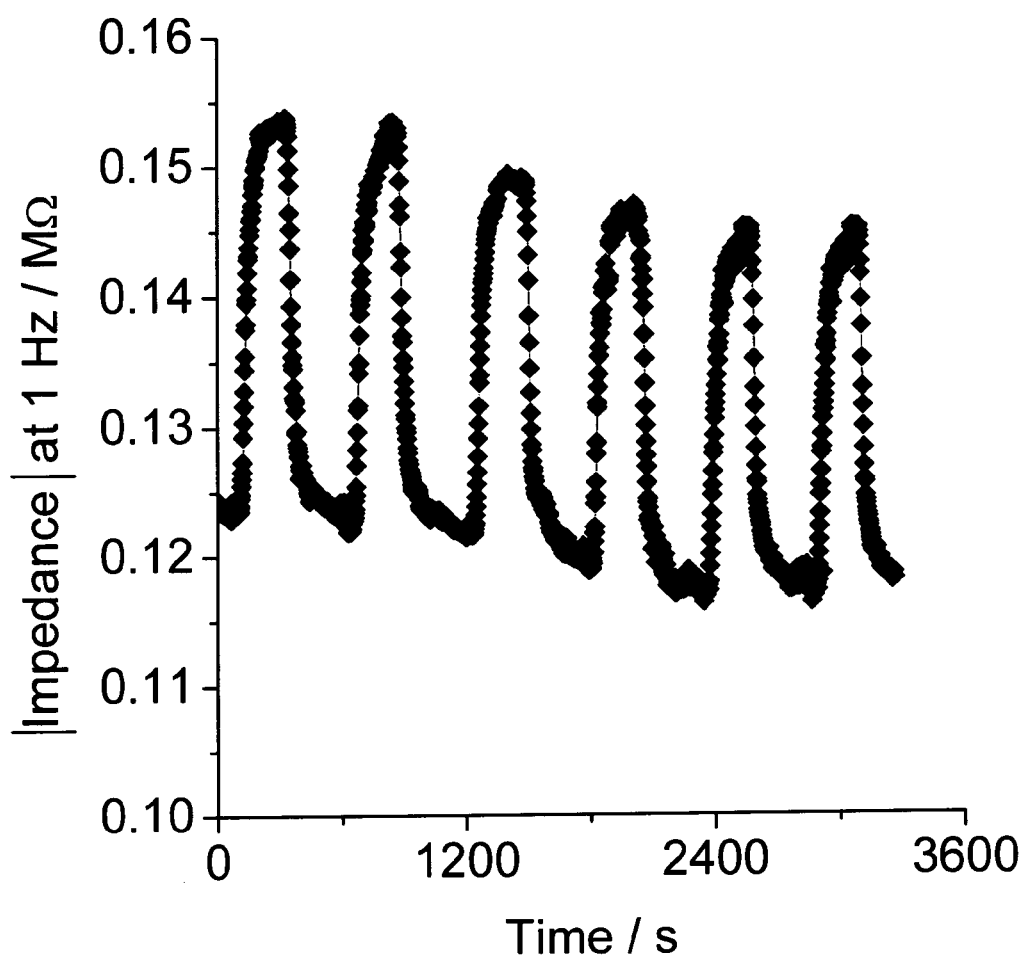
FIG. 7 shows the response curves of chemiresistor band microelectrodes prepared according to example 3, as a function of time upon six repeated exposures to 40 ppm toluene.

In order to minimise the chemiresistor film resistance for a given chemiresistor material compared to the impedance arising from the Cdl due to the area of the conductive electrode pads exposed to the electrolyte solution, other configurations of the conductive electrode pads may be implemented. Non-limiting examples of such preferred implementations are shown in FIG. 3b, FIG. 3c, and FIG. 3d where 14 and 15 are two conductive electrodes that are at least partially coated with a chemiresistor film 16.

The conductive electrode pads may be fabricated by standard photolithographic means, or by electron beam, focussed ion beam or other suitable methods known to those skilled in the art.

The conductive electrode pads may be made from any material that has a sufficiently high electrical conductivity such that its resistance is small compared to the resistance of the chemiresistor thin film and such that it is electrochemically inert under the measurement conditions, that is electrochemically inert when immersed in electrolyte for the period of the measurement. Suitable materials may be inert metals such as gold palladium, platinum, silver, copper, nickel or conductive materials based on conductive carbon such as carbon black.

Gold, silver, palladium and platinum are particularly preferred electrode materials.

Preferably, the electrodes are coated with a dielectric layer. The dielectric layer serves to reduce the capacitance of the double layer capacitor formed between the two electrically conducting electrodes and the electrolyte and therefore increase the impedance of the capacitor.

It is further preferred that the dielectric layer is a thin layer of an inert material that has a dielectric constant that is lower than that of water, is at least partially impermeable towards ions and that is thinner than 2 nanometers.

This thin layer has the effect of decreasing the effective Cdl of the conductive electrode pads exposed to the electrolyte. For instance it is known in the art that while the Cdl of a bare gold surface has values of between 10-40 $\mu F/cm^2$, a gold surface coated with a self-assembled monolayer of hexadecane thiol has a Cdl of 1 $\mu F/cm^2$, i.e. a reduction in the capacitance value of approximately 10, with a concomitant increase in the impedance by a factor of 10.

It is further preferred that this thin layer of an inert material is a self-assembled monolayer formed onto the surface of the gold, silver, palladium or platinum electrode material. Such self-assembled monolayers may be produced from alkane thiols, alkane disulfides, or other sulphur functionalised molecules.

The self-assembled monolayer may include molecules that additionally can be used to anchor the chemiresistor to the surface of the conductive electrode pads either via physical interactions such as hydrophobic interactions, or by chemically bonding parts of the chemiresistor to the self-assembled monolayer.

It is preferred that the substrate onto which the electrodes are produced are an inert non-electrically conducting substrate such as produced from silicon wafers, preferably with a layer of silicon dioxide grown on the surface, glass, or plastics.

It is further preferred that the surface of the substrate is functionalised such that it can be used to anchor the chemiresistor to the surface of the inert non-electrically conducting substrate either via physical interactions such as hydrophobic interactions, or by chemically bonding parts of the chemiresistor to the self-assembled monolayer.

As used in the present invention, the terms "chemiresistor" or "chemiresistor film" preferably refer to a nanoparticle film of conductive nanoparticles that have been capped by a ligand or a mixture of ligands, wherein the thickness of the nanoparticle film is generally less than 100 microns thick and wherein the thickness of the nanoparticle film is at least thick enough such that the nanoparticles form a film that is above the percolation threshold for conduction.

The term "nanoparticle" as used in the present invention comprises a particle that has an average diameter of 1 micron or less and is larger than 1 nm in average diameter. Preferred are particles with diameters less than 100 nm and greater than 2 nm.

A wide variety of electrically conductive materials may be used for the nanoparticles. In particular, it is preferred that the nanoparticles consists of metals or alloys of metals, or core-shell structures of different metals, conductive polymers, or graphitic carbon.

It is particularly preferred that the nanoparticles consist of gold, silver, platinum, or palladium nanoparticles either by themselves or as alloys.

In general nanoparticles are capped, or coated, with a capping agent whose function serves to preserve the stability of the nanoparticles in solution, that is it solubilizes the individual nanoparticles and prevents them from aggregating. The capping agent is generally readily displaced by the ligand used to form the chemiresistor, although in some cases the capping agent may itself act as a ligand.

The term "ligand" as used in the present invention denotes a molecule with one or more binding groups capable of physically or chemically binding to the nanoparticle, and with one or more additional functional groups capable of physically or chemically binding to an analyte molecule.

Ligand binding groups suitable for binding to nanoparticles may include one or more thiol groups, disulfide groups, sulphide groups, phosphine groups, or amine groups.

Functional groups capable of chemically or physically binding to the analyte molecule will depend on the type of analyte that is to be detected. Thus ligands possessing hydrophobic groups may be useful in binding hydrophobic analytes, ligands possessing carboxylic acid groups may be useful in binding analytes containing basic groups such as amines, ligands possessing amine groups may be useful in binding analytes containing carboxylic acids, ligands possessing boronic acids may be useful in binding to analytes containing 1,2-diols, ligands possessing amino acids, peptide, DNA, cyclams, crown ether derivatives and other metal binding groups may be advantageous in binding to analytes that are cations or anions and in particular are heavy metal ions such as copper, iron, cadmium, mercury, zinc ions.

Functional groups capable of chemically or physically binding to the analyte molecule may include but is not limited to hydrocarbon groups such as cyclic or acyclic alkanes, aromatic groups (either single or polyaromatic groups); groups capable of forming hydrogen bonds such as hydroxyl, amine, carboxylic acid, ester, or ether groups; basic groups such as amines; acidic groups such as carboxylic acids, sulfonic acids, phosphonic acids; positively charged groups such as ammonium or pyridinium groups; negatively charged groups such as salts of acids such as carboxylate, sulfonate or phosphonate groups; boronic acid groups that interact with carbohydrates; amino acid or peptide groups; DNA or RNA fragments; crown ethers or their derivatives.

Preferred ligands may include but are not limited to alkane thiols such as ethane thiol, propane thiol, butane thiol, pentane thiol, hexane thiol, heptane thiol, octane thiol, nonane thiol, decane thiol, undecane thiol, dodecane thiol, tridecane thiol, tetradecane thiol, pentadecane thiol, hexadecane thiol, heptadecane thiol, octadecane thiol, phytanyl thiol, thiophenol, benzyl mercaptan, p-thiocresol, 2-methylbenzenethiol, 3-methylbenzenethiol, mercaptopyridine, mercaptobenzoic acid, mercaptophenylboronic acid, hydroxythiophenol, aminothiophenol, methoxythiophenol, alpha-omega hydroxy alkane thiols, alpha-omega amino alkane thiols, alpha-omega carboxyl alkane thiols, thiol substituted oligoethylene glycols including the monothiol of ethylene glycol, triethylene glycol, tetraethylene glycol, pentaethylene glycol, or hexaethylene glycol, alkane dithiols such as 1,2-ethanedithiol, 1,3-propanedithiol, 1,4-butanedithiol, 1,5-pentanedithiol, 1,6-hexanedithiol, 1,7-hepatnedithiol, 1,8-octanedithiol, 1,9-nonanedithiol, 1,10-decanedithiol, 1,11-undecanedithiol, 1,12-dodecanedithiol, 1,3-tridecanedithiol, 1,14-tetradecanedithiol, 1,5-pentadecanedithiol, 1,16-hexadecanedithiol, 1,17-heptadecanedithiol, 1,18-octadecanedithiol, cysteine, 4-tert-butylbenzenethiol, 2-naphthalenethiol, 4-tert-butylbenzylmercaptan, cyclopentylmercaptan, cyclohexylmercaptan, 2,3,5,6-tetrafluorbenzenethiol, 3,4-difluorothiophenol, 4-bromobenzenethiol, 4-chlorobenzenethiol, 4-fluorobenzenethiol, 4-nitrothiophenol, 4-methoxybenzylmercaptan 2-phenylethanethiol.

As will be readily appreciated by those skilled in the art, the symmetrical or mixed disulfides of the above compounds may be readily produced from oxidation of the appropriate thiol and may also be used.

Chemiresistor film may be prepared by a number of methods such as spray painting, screen printing, solution deposition, layer-by layer depositions, stamping, painting, spin coating, drop deposition or printing. In particular, various methods of printing exist that are particularly suitable for producing chemiresistor thin films based on solutions of nanoparticles and solutions of ligands. Such printing methods include inkjet printing using thermal printing or piezoelectric printing methods, as well as gravure, and off-set printing.

A particularly preferred method of producing chemiresistors is the use of inkjet printing, either thermal (bubblejet) printing or piezoelectric printing techniques.

Piezoelectric printing techniques are particularly preferred.

In a further preferred embodiment of the present invention, a solution of the nanoparticles is printed, said nanoparticles are stabilized with a capping agent that is readily displaced by one or more ligand groups. The nanoparticle film is subsequently exposed to one or more ligand groups, either sequentially or as a mixture, in order to form the chemiresistor.

It is further preferred that the capping agent is N, N'-dimethylamino pyridine (DMAP).

It is further preferred that a solution of the nanoparticles is printed, said nanoparticles are stabilized with a capping agent that is readily displaced by one or more ligand groups and that said ligand groups are also deposited onto the printed nanoparticles by inkjet printing, wherein the nanoparticle film is functionalised by the ligands in-situ on the substrate.

It is further preferred that a solution of the nanoparticles is printed by inkjet or micropipette droplet printing, the nanoparticles being gold nanoparticles of between 4 to 8 nm in diameter, with DMAP as the capping agent, formulated as an ink in water at a concentration of between 1 to 10% weight/volume, said aqueous solution containing N-methyl-2-pyrrolidone (NMP) at between 1 to 10% weight/volume concentration. The nanoparticle film is subsequently exposed to one or more ligand groups, either sequentially or as a mixture, in order to form the chemiresistor.

It is particularly preferred that a solution of the nanoparticles is printed by inkjet or micropipette droplet printing, the nanoparticles being gold nanoparticles of between 4 to 8 nm in diameter, with DMAP as the capping agent, formulated as an ink in water at a concentration of 1% weight/volume, said aqueous solution containing N-methyl-2-pyrrolidone (NMP) at 4% weight/volume concentration. The nanoparticle film is subsequently exposed to one or more ligand groups, either sequentially or as a mixture, in order to form the chemiresistor.

In a preferred embodiment of the present invention mixtures of ligands with different functional groups are used within the same chemiresistor nanoparticle film in order to tailor the chemiresistors interactions with the analyte, thus enabling the formation of different chemiresistors with different selectivities and sensitivities towards various analytes.

As will be appreciated by those skilled in the art, combinatorial synthesis methods and high-throughput screening methods, wherein different mixtures of ligands are used to functionalised the nanoparticle films and large numbers of such functionalised nanoparticle films are subsequently interrogated for their response towards analyte solutions of interest, may be used to determine the optimal types and ratios of ligands required in order to optimise the response of the chemiresistor array towards different analytes.

The chemiresistors as described by way of the present invention may be used either singly or in the form of arrays of chemiresistors wherein each chemiresistor may respond differently to the presence of a particular analyte in the test solution and the various changes in resistance are analysed by standard analytical methods such as principal component analysis in order to obtain information as to the presence or absence of a particular analyte and its concentration in the test solution.

In one embodiment, the present invention provides a nanoparticle film whose resistance properties change on exposure to an analyte in an electrolyte solution, additionally electrical contact being made to said nanoparticle film by two electrically conductive electrodes in order to connect the nanoparticle film to a measuring device used to determine the electrical impedance properties of the nanoparticle film, and wherein the area of the electrically conductive electrodes being exposed to the electrolyte solution is small enough such that the double layer capacitance formed between the electrically conductive electrodes and the electrolyte is small and hence the impedance is higher than the impedance of the nanoparticle film either before or after exposure to the analyte contained in the electrolyte solution.

In a third aspect, the present invention provides a method for determining the partition coefficient of an analyte using the chemiresistor-based sensor of the first aspect, said method comprising the steps of:

(i) contacting said chemiresistor film with two or more solutions of said analyte wherein said two or more solutions of said analyte are of known but different concentrations;

(ii) measuring the change in impedance of said chemiresistor film for each of said two or more solutions;

(iii) fitting a line to the log-log plot of change in the impedance of the nanoparticle film versus concentration of said analyte;

(iv) calculating the value of the logarithm of the slope of said fitted line;

(v) comparing the value of the logarithm of the slope of said fitted line to a standard curve correlating the logarithm of said slope of said fitted line to the logarithm of the partition coefficient to thereby determine said partition coefficient of said analyte.

The standard curve can be constructed by carrying out steps (i) to (iv) for two or more analytes having known partition coefficients.

In one embodiment, the partition coefficient is a hexane/water partition coefficient.

In another embodiment, the partition coefficient is an octane/water coefficient.

Preferably, said two or more solutions of analyte are aqueous solutions of said analyte.

In a further embodiment, there is provided a method of producing a chemiresistor based sensor according to the first aspect, said method comprising the steps of:

(i) printing an aqueous solution of DMAP-Au nanoparticles onto a band microelectrode;

(ii) allowing said printed DMAP-Au nanoparticle solution to dry;

(iii) and subsequently exposing said dry DMAP-Au nanoparticle film to an organic solvent solution containing at least one thiol or disulfide containing ligand.

In a yet further embodiment, there is provided a method of producing a chemiresistor based sensor according to the first aspect, said method comprising the steps of:

(i) printing an aqueous solution of DMAP-Au nanoparticles containing 4% w/v N-methyl-2-pyrrolidone onto a band microelectrode;

(ii) allowing said printed DMAP-Au nanoparticle solution to dry;

(iii) and subsequently exposing said dry DMAP-Au nanoparticle film to an organic solvent solution containing at least one thiol or disulfide containing ligand.

In order that the nature of the present invention may be more clearly understood preferred forms thereof will now be described with reference to the following non-limiting Examples.

EXAMPLES

Example 1

Synthesis of DMAP-Au gold nanoparticles

Gold nanoparticles were synthesised following the Brust method (Brust, M. et al. J. Chem. Soc. Chem. Commun 1994, 801-802) and transferred to the aqueous phase following the method by Gittins (Gittins, D. I.; Caruso, F. Angew. Chemie Int. Ed. 2001, 40, 3001-3004). Briefly, a solution of $HAuCl_4$ was added to a stirred solution of tetraoctylammonium bromide (TOAB) in toluene. Stirring was continued for 10 min and was followed by the addition of sodium borohydride which resulted in reduction of the gold. After 2 hours, the lower aqueous phase was removed and the toluene phase was subsequently washed twice with sulfuric acid, twice with sodium carbonate and twice with water. For the spontaneous and complete phase transfer of the nanoparticles from the organic to the aqueous phase, an aqueous solution of dim-ethylamino pyridine (DMAP) was added to the as-prepared nanoparticles. The solution containing the DMAP coated gold nanoparticles (DMAP-Au) was then evaporated under a gentle stream of nitrogen to leave a gold ink powder. The dried DMAP-Au powder was stored at −20° C. and an aqueous solution of DMAP-Au was prepared as required. All DMAP-Au solutions were filtered with a 0.22 µm Millex® GS filter unit (Millipore, Australia) prior to use.

Example 2

Preparation of Band Microelectrodes

Glass microscope slides were cleaned and coated by vacuum evaporation with an adhesion layer of chromium, followed by a layer of gold. Standard photolithography techniques and etching techniques were used to produce a band microelectrode as shown in FIG. 1 consisting of two parallel gold electrodes that were 3 mm long, 5 microns wide and separated by a 5 micron gap between the two gold electrodes. An array of six such band microelectrodes were produced on each glass slide.

The glass slides patterned with the six gold band microelectrodes were pre-treated with a silylating agent (mercaptopropyl triethoxysilane, MPTES) prior to gold nanoparticle deposition for better adhesion of the nanoparticle to the glass and the electrode surface. Thus, the glass slides were immersed in a solution containing 2% v/v MPTES in toluene for two hours, followed by rinsing with copious amounts of toluene and drying under a gentle stream of nitrogen. The treated glass slides were then baked in an oven at 110° C. for one hour.

Example 3

Formation of Chemiresistor Sensors Using Inkjet Printing Using a 1% w/v DMAP-Au Solution Inkjet printing of DMAP-Au solution was carried using an Autodrop printing system (from Microdrop Technologies, Germany). The printhead used was an AD-K-501 micropipette (25 µL holding volume, 70 µm diameter nozzle). The micropipette was filled with a 1% w/v DMAP-Au aqueous solution that had been placed in a 96-well plate positioned on the printing platform. A rectangular voltage pulse was applied to dispense droplets from the micropipette nozzle with a typical droplet volume of 180 pL. The drop frequency was set at 200 Hz and the tip of the micropipette was positioned 1 mm above the substrate during the printing process. The band microelectrodes were prepared as per example 2 and were positioned on the inkjet printer platform in a suitable position.

Subsequently, 10 drops of a 1% w/v DMAP-Au aqueous solution were then inkjet-printed over each of the six band microelectrodes on the glass slide, and the solvent was allowed to evaporate. This resulted in a circular nanoparticle film area approximately 300 microns in diameter, which coated a portion of both bands of the band electrode. Atomic force microscopy analysis of the nanoparticle film indicated that the nanoparticle film morphology showed a "coffee ring" effect wherein the circumference of the nanoparticle film was significantly higher than the centre of the nanoparticle film.

After two hours, the microelectrodes, with the DMAP-Au deposited, were functionalised with 1-hexanethiol by exposing the electrodes to 1-hexanethiol vapour for 30 min. Following this time, the microelectrode array was removed from the 1-hexanethiol vapour, allowed to stand for a further 30 minutes and then rinsed with water to form the functional chemiresistor array.

Example 4

Formation of Chemiresistor Sensors Using Inkjet Printing Using a 1% w/v DMAP-Au Solution Containing 4% w/v N-methyl-2-pyrrolidone Inkjet printing of DMAP-Au solution was carried using an Autodrop printing system (from Microdrop Technologies, Germany). The printhead used was an AD-K-501 micropipette (25 µL holding volume, 70 µm diameter nozzle). The micropipette was filled with a 1% w/v DMAP-Au aqueous solution containing 4% w/v N-methyl-2-pyrrolidone that had been placed in a 96-well plate positioned on the printing platform. A rectangular voltage pulse was applied to dispense droplets from the micropipette nozzle with a typical droplet volume of 180 pL. The drop frequency was set at 200 Hz and the tip of the micropipette was positioned 1 mm above the substrate during the printing process. The band microelectrodes were prepared as per example 2 and were positioned on the inkjet printer platform in a suitable position.

Subsequently, 10 drops of a 1% w/v DMAP-Au aqueous solution containing 4% w/v N-methyl-2-pyrrolidone were then inkjet-printed over each of the six band microelectrodes on the glass slide, and the solvent was allowed to evaporate. This resulted in a circular nanoparticle film area approximately 300 microns in diameter, which coated a portion of both bands of the band electrode. Atomic force microscopy analysis of the printed nanoparticle film indicated a uniform flat disk-shaped film with a much reduced "coffee-ring" effect compared to chemiresistors prepared according to example 3.

After two hours, the microelectrodes, with the DMAP-Au deposited, were functionalised with 1-hexanethiol by exposing the electrodes to 1-hexanethiol vapour for 30 min. Following this time, the microelectrode array was removed from the 1-hexanethiol vapour, allowed to stand for a further 30 minutes and then rinsed with water to form the functional chemiresistor array Example 5

Determination of Hydrocarbon Analytes in Concentrated Electrolyte Solution

Figure 8:
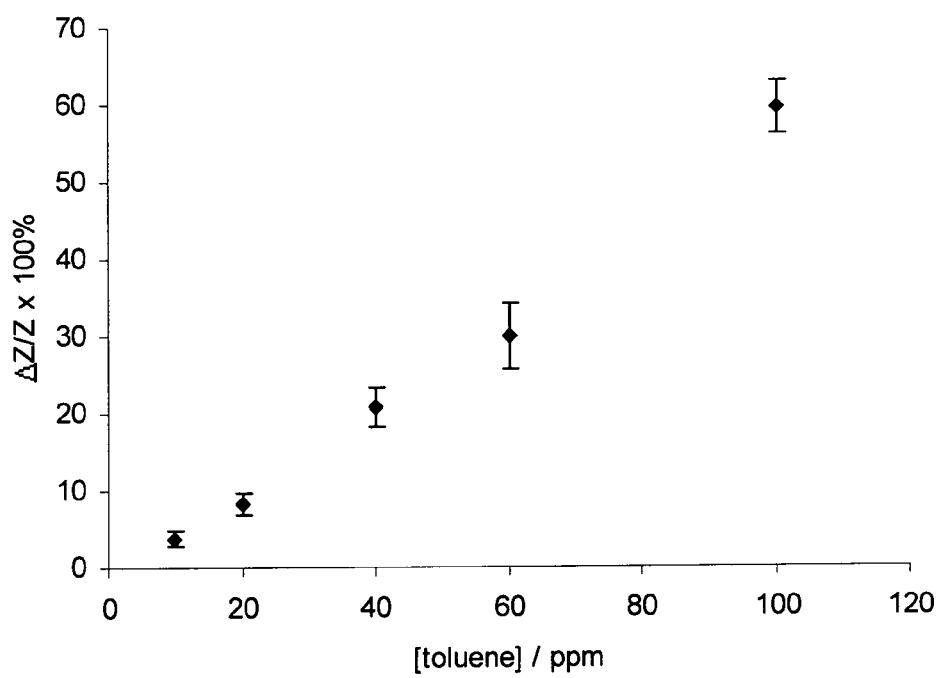
FIG. 8 shows the relative change in impedance of chemiresistor band microelectrodes prepared according to example 4, as a function of concentration of toluene.

The chemiresistor array as prepared in examples 3 or 4, was placed in a flow cell such that the nanoparticle chemiresistor was exposed to the electrolyte solution and 1M KCl solution was pumped across the chemiresistor using a syringe pump wile determining the impedance at 1 Hz using a PARRSTAT 2273 Electrochemical Impedance Bridge. After determining the baseline impedance response, a solution of 1M KCl containing different amounts of either toluene, dichloromethane or ethanol as the analyte was pumped across the chemiresistor and the impedance response was monitored. In a typical procedure, 1 M KCl solution was flowed over the sensor surface (at 0.66 mL/min) for at least 1 min prior to switching the flow solution to the analyte and 1 M KCl solution for 4 min. After this time, the analyte was removed by switching back to a 1 M KCl solution. At suitable analyte concentrations an increase in the low frequency impedance was observed in response to the presence of the analyte. Results shown in FIGS. 4 to 7 relate to chemiresistors made according to examples 3, while FIG. 8 relates to chemiresistors made according to example 4.

Example 6

Determination of Hydrocarbon Analytes in Aqueous Solution Using Direct Current (dc) Measurement A chemiresistor array was prepared as in example 1,2, and 4 except that a Biodot XYZ 3200 printer was used to deposit 30 drops of a 1% w/v DMAP-Au aqueous solution containing 4% w/v N-methyl-2-pyrrolidone over each of the six band electrodes. The volume of each drop was approximately 10 nL. The band electrodes consisted in 10 interdigitated parallel gold electrodes that were 3 mm long, 5 microns wide and separated by a 5 micron gap between the two gold electrodes. After two hours, the microelectrodes, with the DMAP-Au deposited, were functionalised with 1-hexanethiol by exposing the electrodes to 1-hexanethiol vapour for 30 min. Following this time, the microelectrode array was removed from the 1-hexanethiol vapour, allowed to stand for a further 30 minutes and then rinsed with ethanol to form the functional chemiresistor array.

The chemiresistor array was then placed in a flow cell and water was flowed across the nanoparticle chemiresistor using a small pump such as a peristaltic pump or a small vacuum pump. A computer controlled 8-position valve from Hamilton Inc was used to switch between aqueous solutions containing the analyte and aqueous solutions without analyte. A dc voltage of 100 mV was applied across the chemiresistor using a potentiostat and the current was measured with time. As expected for a capacitor, on application of the 100 mV potential the initial current spike decayed approximately exponentially to a steady value. From Ohm's law the resistance of the nanoparticle chemiresistor film could be obtained or changes in current on exposure of the chemiresistor to aqueous solution containing the analyte could be used to directly determine the percentage change in current due to exposure of the chemiresistor to the analyte.

After determining the baseline current, an aqueous solution containing different amounts of toluene, m-dichlorobenzene, 1-propanol, or nitrobenzene were pumped across the chemiresistor while changes in the current were monitored. In a typical procedure, aqueous solutions without analyte was pumped across the chemiresistor for 2 minutes, followed by the aqueous solution containing the analyte for 2 minutes. In the current example, the changes in the current were analysed by correcting for baseline drift of the chemiresistor response immediately prior to analyte response, and then the percentage change for each analyte at each concentration measured was calculated. The chemiresistor response towards m-dichlorobenzene in water (% change in current, (analyte concentration)) was: 0.23% (0.1 ppm), 0.37% (0.2 ppm), 0.69% (0.5 ppm), 1.18% (1 ppm), 2.36% (2 ppm), 5.63% (5 ppm), 10.19% (10 ppm). The chemiresistor response towards toluene in water (% change in current, (analyte concentration)) was: 0.14% (0.1 ppm), 0.22% (0.2 ppm), 0.29% (0.5 ppm), 0.43% (1 ppm), 0.87% (2 ppm), 1.88% (5 ppm), 3.43% (10 ppm). The chemiresistor response towards nitrobenzene in water (% change in current, (analyte concentration)) was: 0.18% (2 ppm), 0.30% (5 ppm), 0.52% (10 ppm), 0.93% (20 ppm). The chemiresistor response towards 1-propanol in water (% change in current, (analyte concentration)) was: 0.49% (2000 ppm), 1.06% (5000 ppm), 1.90% (10000 ppm), 3.83% (20000 ppm).

Example 7

Figure 9:
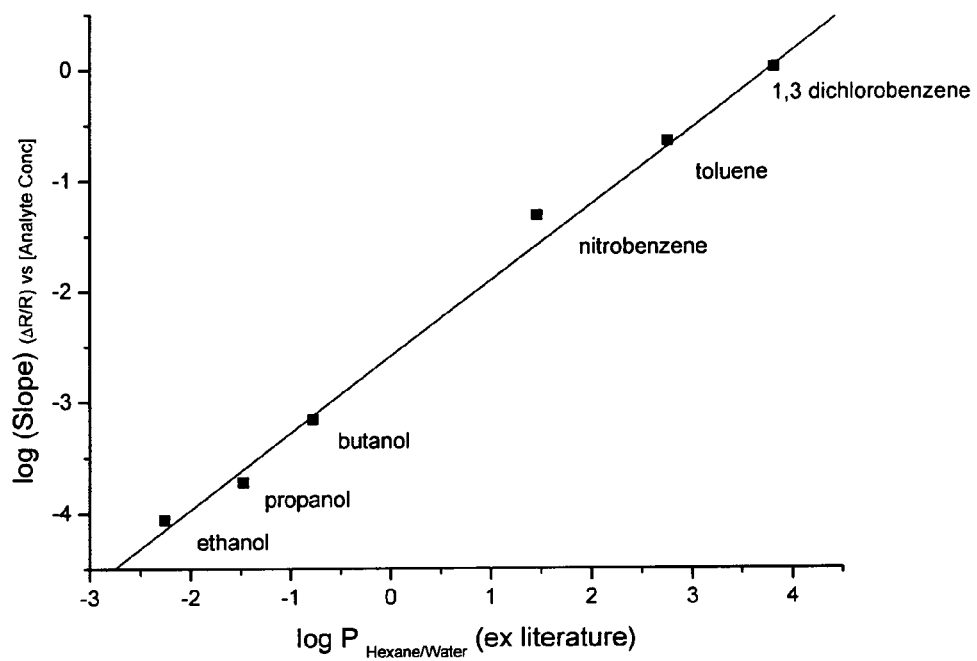
FIG. 9 shows the correlation between the logarithm of the slope of the chemiresistor response towards organic analytes and the logarithm of known hexane/water partition coefficients

Correlation Between the Chemiresistor Sensor Response Towards Organic Analytes in Water and the Hexane/Water Partition Coefficient A chemiresistor array was prepared as described in example 6 and the chemiresistor response towards m-dichlorobenzene, toluene, nitrobenzene, ethanol, 1-propanol, and 1-butanol in water was determined. A line was fitted (least squares fit) to the log-log plot of % change in chemiresistor response versus concentration of analyte in water, in the % change range of between 0.3% to 5% change. A plot of the logarithm of the slope of the fitted line versus the literature values of the logarithm of the hexane/water partition coefficient (logP) obtained from P. Ruelle, *Chemosphere*, 40 (2000) pg 457-512 is shown in FIG. 9. A linear correlation (correlation coefficient 0.997) was found between the chemiresistor response towards the analyte in water and the hexane/water partition coefficient. This shows that the chemiresistors described herein can be used to determine logP values of organic molecules.

Example 8

Changing the Chemiresistor Response Towards Different Analytes Using Mixtures of Different Thiol Ligands A chemiresistor array was prepared as in example 1,2, and 4 except that the DMAP-Au nanoparticle films were not functionalised by exposing to 1-hexanethiol vapour, but were functionalised by immersing the DMAP-Au nanoparticle films into acetonitrile solutions containing various ratios of 1-hexanethiol and 4-mercaptophenol. The mol % ratio of 1-hexanethiol to 4-mercaptophenol was varied from 100:0, 90:10, 80:20, 70:30, 60:40, 50:50, 40:60, 30:70, 20:80, 10:90, 0:100. Immersion time in the thiol containing acetonitrile solution was 1 hour and following this time the chemiresistors array was rinsed with acetonitrile and then water. The chemiresistor response towards aqueous solutions containing toluene and ethanol was then determined as for example 5 except that deionised water was used instead of 1M KCl solution. As will be appreciated to those skilled in the art, the basic principle of functionalizing arrays of chemiresistors with different ratios of different ligands and subsequently determining the chemiresistor response towards analytes of interest is essentially a combinatorial material synthesis and high-throughput screening process and can be readily expanded and automated to scan large numbers of combinations of different ligands.

The response of the chemiresistor arrays towards aqueous solutions of toluene (100 ppm) is given in Table 1, and the response of the chemiresistor arrays towards aqueous solutions of ethanol (10000 ppm) is given in Table 2. As can be seen for ethanol a maximal response is seen at a 1-hexanethiol:4-mercaptophenol ratio of about 60:40; whereas a maximal response towards toluene is seen at a 1-hexanethiol:4-mercaptophenol ratio of 100:0.

TABLE 1

Response to 100 ppm toluene dissolved in water

| 1-hexanethiol/ mol % | 4-mercaptophenol/ mol % | % change in \|impedance\| |
|---|---|---|
| 0 | 100 | 0.38 ± 0.03 |
| 10 | 90 | 0.85 ± 0.26 |
| 20 | 80 | 1.06 ± 0.20 |
| 30 | 70 | 2.75 ± 0.28 |
| 40 | 60 | 3.16 ± 0.72 |
| 50 | 50 | 3.60 ± 0.43 |
| 60 | 40 | 6.19 ± 0.40 |
| 70 | 30 | 8.00 ± 0.55 |
| 80 | 20 | 15.8 ± 1.85 |
| 90 | 10 | 20.2 ± 1.06 |
| 100 | 0 | 37.0 ± 2.46 |

TABLE 2

Response to 10000 ppm ethanol dissolved in water

| 1-hexanethiol/ mol % | 4-mercaptophenol/ mol % | % change in \|impedance\| |
|---|---|---|
| 0 | 100 | 0.63 ± 0.11 |
| 10 | 90 | 0.80 ± 0.16 |
| 20 | 80 | 1.25 ± 0.26 |
| 30 | 70 | 1.44 ± 0.21 |
| 40 | 60 | 1.58 ± 0.27 |
| 50 | 50 | 1.73 ± 0.19 |
| 60 | 40 | 2.02 ± 0.26 |
| 70 | 30 | 1.99 ± 0.17 |
| 80 | 20 | 1.88 ± 0.14 |
| 90 | 10 | 1.70 ± 0.21 |
| 100 | 0 | 0.78 ± 0.18 |

Throughout this specification, the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of the matters form part of the prior art base or were common general knowledge in the field relevant to present invention as it existed in Australia or elsewhere before the priority date of each claim of this application.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

CROSS-REFERENCE TO RELATED APPLICATIONS

The present application claims priority from Australian Provisional Patent Application No 2007900501 filed on 2 Feb. 2007, the content of which is incorporated herein by reference.

The invention claimed is:

1. A sensor for measuring the presence or amount of analyte in an electrolyte solution of predetermined permittivity $\in$; said sensor comprising:
   (i) two electrically conducting electrodes on an electrically insulating substrate,
      and separated by a distance L, where L is between 10 nm and 10 μm;
   (ii) a chemiresistor film, wherein the impedance of the chemiresistor film changes in the presence of an analyte;
   wherein the chemiresistor film is in contact with the electrodes;
   wherein the sensor comprises a voltage means configured to provide a low frequency f<$f_0$=100 Hz signal or DC voltage across the electrodes;
   wherein the apparent area A of a double layer capacitor formed by the electrodes and the chemiresistor film in the electrolyte solution is less than half of $A_0$, where $$A_0 = \frac{d}{2\pi f_0 \varepsilon \varepsilon_0 R}$$

and
   wherein $\in_0$ and d are predetermined and R is the resistance of the electrodes and the chemiresistor film in the electrolyte solution.

2. A sensor according to claim 1 wherein said chemiresistor film is a nanoparticle film comprising a film of conductive nanoparticles that have been capped by a ligand or a mixture of ligands.

3. A sensor according to claim 2 wherein said conductive nanoparticles are made from gold, silver, platinum or palladium.

4. A sensor according to claim 2 wherein said conductive nanoparticles are made from gold, or palladium.

5. A sensor according to claim 1 wherein the ligands possess at least one thiol or disulfide group.

6. A sensor according to claim 5 wherein the ligands are alkanethiols or alkanedisulfides, or mixtures thereof, with alkane groups of between 2 carbons and 16 carbons in length.

7. A sensor according to claim 5 wherein the ligands are alpha-omega-functionalised alkanethiols or alpha-omega-functionalised alkanedisulfides, or mixtures thereof, with alkane groups of between 2 carbons and 16 carbons in length.

8. A sensor according to claim 5 wherein the ligands are thiols or disulfides, or mixtures thereof, containing at least one functionalized benzene group.

9. A sensor according to claim 5 wherein mixtures of two or more different ligands are used.

10. A chemiresistor-based sensor according to claim 1 wherein the voltage means is configured to provide a variable voltage signal.

11. A sensor according to claim 10 wherein the voltage means is configured to provide a sinusoidal alternating current signal.

12. A sensor according to claim 1 wherein the voltage means is configured to provide a direct current signal.

13. A sensor according to claim 1 wherein the two electrically conducting electrodes are coated with a dielectric layer.

14. A sensor according to claim 13 wherein the dielectric layer comprises in a self-assembled monolayer of mercaptopropyl triethoxysilane, or an alkanedithiol wherein the alkane group is a linear alkane chain between 2 carbon and 30 carbons long.

15. A sensor according to claim 13 wherein the dielectric layer comprises in a self-assembled monolayer of an alkanedithiol wherein the alkane group is a linear alkane chain between 2 carbon and 18 carbons long.

16. A sensor according to claim 1 wherein said two electrically conductive electrodes are made from two or more parallel band electrodes.

* * * * *